United States Patent [19]
Miyashiro et al.

[11] 4,263,398
[45] Apr. 21, 1981

[54] 9-(P-DIETHYLAMINOPHENYL)-9-CHLORO-10-PHENYLACRIDAN AGAR MEDIUM

[75] Inventors: James J. Miyashiro, Woodstock, Ill.; Lorraine M. Marold, Norwich, N.Y.

[73] Assignee: Morton-Norwich Products, Inc., Norwich, N.Y.

[21] Appl. No.: 67,610

[22] Filed: Aug. 20, 1979

Related U.S. Application Data

[63] Continuation of Ser. No. 953,447, Oct. 23, 1978, abandoned.

[51] Int. Cl.³ .............................................. C12Q 1/04
[52] U.S. Cl. ..................................... 435/34; 435/875; 424/257; 546/104
[58] Field of Search .......................... 546/104; 424/257; 435/32, 34, 87 S

[56] References Cited

U.S. PATENT DOCUMENTS

| 2,645,594 | 7/1953 | Tabern | 424/257 |
| 3,122,480 | 2/1964 | Turner et al. | 435/875 X |
| 4,063,015 | 12/1977 | Mallams | 435/32 X |
| 4,072,573 | 2/1978 | Aldridge et al. | 435/34 |
| 4,146,433 | 3/1979 | Masuda et al. | 435/32 |

OTHER PUBLICATIONS

Glen et al., *Chemische Berichte*, 73B, pp. 757–761 (1940).

*Primary Examiner*—Thomas G. Wyse
*Attorney, Agent, or Firm*—Anthony J. Franze

[57] ABSTRACT

The compound 9-(p-diethylaminophenyl)-9-chloro-10-phenylacridan is a useful antibacterial agent.

1 Claim, No Drawings

9-(P-DIETHYLAMINOPHENYL)-9-CHLORO-10-PHENYLACRIDAN AGAR MEDIUM

This is a continuation of application Ser. No. 953,447 filed Oct. 23, 1978 now abandoned.

This invention is concerned with the chemical compound 9-(p-diethylaminophenyl)-9-chloro-10-phenylacridan. It is a useful antibacterial agent. Its antibacterial spectrum encompasses both Gram-negative and Gram-positive bacteria. Such antibacterial efficacy makes it useful as the active ingredient in compositions designed to inhibit or eradicate bacterial growth. Such compositions include pharmaceutical dosage forms such as creams, ointments, gels, solutions, powders and the like, or it may be incorporated in various objects such as synthetic resins, paints, lacquers and the like to exert a protective effect against bacterial attack or spoilage.

Table I herebelow reflects the antibacterial potency and spectrum of the compound of this invention using the commonly employed serial dilution technique for determining antibacterial activity:

TABLE I
ANTIBACTERIAL ACTIVITY (MIC) AGAINST SELECTED MICROORGANISMS BY A SERIAL DILUTION METHOD IN BRAIN HEART INFUSION BROTH

| Microorganism | Culture Code | No. | MIC* ($\mu$g/ml) |
|---|---|---|---|
| (Gram-Negative Fermentative Bacilli) | | 34 | 6.2 |
| | | 54 | 12.5 |
| | | 63 | 12.5 |
| Enterobacter aerogenes | Ae- | 67 | 12.5 |
| Enterobacter cloacae | | 8 | 25 |
| | | 62 | 12.5 |
| | | 65 | 25 |
| | | 66 | 12.5 |
| Escherichia coli | | 2 | 0.19 |
| | | 90 | 0.38 |
| | Es- | 144 | 1.5 |
| | | 145 | 3.1 |
| | | 168 | 1.5 |
| Klebsiella pneumoniae | Kl- | 20 | 6.2 |
| | | 23 | 12.5 |
| Proteus mirabilis | | 91 | 3.1 |
| | | 92 | 3.1 |
| | | 112 | 3.1 |
| | | 113 | 3.1 |
| | | 115 | 3.1 |
| Proteus morganii | Pr- | 100 | 1.5 |
| | | 103 | 1.5 |
| Proteus rettgeri | | 98 | 1.5 |
| | | 99 | 0.75 |
| Proteus vulgaris | | 2 | 0.75 |
| | | 12 | 1.5 |
| | | 93 | 1.5 |
| | | 110 | 0.75 |
| Salmonella cholerae-susi | | C-104 | 12.5 |
| Salmonella paratypniA | | A-16 | 3.1 |
| Salmonella pullorum | Sa- | D-91 | 12.5 |
| Salmonella schotmuelleri | | B-205 | 25 |
| Salmonella typhi | | D-13 | 0.75 |
| Salmonella typhimurium | | B-203 | 0.75 |
| Serratia marcescens | Se- | 2 | 3.1 |
| | | 12 | 6.2 |
| Shigella dysenteriae | | | |
| Shigella flexneri | Sh- | 382 | 0.38 |
| | | 378 | 0.38 |
| (Gram-Negative Non-Fermentative Bacilli) | | | |
| Acinetobacter calcoaceticus var anitratus | Hv- | 1 | 3.1 |
| Acinetobacter calcoaceticus var lwoffi | Mm- | 3 | 0.024 |
| Alcaligenes faecalis | Al- | 1 | 6.2 |
| | | 10 | 100 |
| | | 26 | 100 |

TABLE I-continued
ANTIBACTERIAL ACTIVITY (MIC) AGAINST SELECTED MICROORGANISMS BY A SERIAL DILUTION METHOD IN BRAIN HEART INFUSION BROTH

| Microorganism | Culture Code | No. | MIC* ($\mu$g/ml) |
|---|---|---|---|
| | | 44 | 100 |
| | | 61 | 100 |
| | | 82 | 100 |
| | | 86 | 100 |
| | | 87 | 100 |
| Pseudomonas aeruginosa | Ps- | 88 | 50 |
| | | 89 | 100 |
| | | 90 | 100 |
| | | 91 | 50 |
| | | 92 | >100 |
| | | 93 | 100 |
| Pseudomonas diminuta (Gram-Variable Bacillus) | | 94 | 0.75 |
| Haemophilus vaginalis (Gram-Positive Cocci) | He- | 127 | 0.024 |
| Staphylococcus aureus | | 12 | 0.024 |
| | | 246 | 0.006 |
| | | 253 | 0.003 |
| | | 256 | 0.012 |
| Staphylococcus cohnii | Mi- | 252 | 0.75 |
| Staphylococcus epidermidis | | 247 | 0.006 |
| | | 249 | 0.012 |
| | | 262 | 0.006 |
| | | 263 | 0.006 |
| Streptococcus agalactiae | | B-86 | 0.38 |
| Streptococcus faecium | St- | D-37 | 0.38 |
| Streptococcus pyrogenes (Gram-Positive Bacilli) | | A-18 | 0.19 |
| Bacillus cereus var mycoides | Ba- | 31 | 0.048 |
| Bacillus subtilis | | 4 | 0.024 |
| Brevibacterium ammoniagenes | Bv- | 1 | 0.012 |
| Corynebacterium liquefaciens | Co- | 11 | 0.048 |
| Corynebacterium xerosis | | 14 | 0.38 |

*MIC = Minimal inhibitory concentration

As is evident from Table I above, the bacterial pathogen Pseudomonas aeruginosa is unaffected by realistic dosage amounts of the compound of this invention. Its failure to inhibit this pathogen at such levels is an attribute rather than a detriment, for its ability to inhibit other commonly prevalent bacteria enables it to be used as the active ingredient in a selective medium such as that disclosed in USP XIX when it is desired to detect Pseudomonas aeruginosa to the exclusion of other bacterial species. The ability of the compound of this invention to exert such bacterial selectivity is reflected in Table II herebelow wherein in addition to Pseudomonas aeruginosa less susceptible Enterobacter and Serratia strains are tested:

TABLE II
EFFECT OF CONCENTRATION ON SELECTIVITY OF BASAL AGAR MEDIUM FOR PSEUDOMONAS AERUGINOSA UPON CHALLENGE INOCULATION WITH SOME NON-PSEUDOMONAO STRAINS AS DETERMINED BY AVERAGE COLONY COUNTS

| Test Microoganism | Culture Code | No. | Selective ($\mu$g/ml) Basal Medium 20 | 25 | 30 | Non-Selective TSA[1] Control |
|---|---|---|---|---|---|---|
| | | 10 | 295 | 265 | 308 | 283 |
| | | 26 | 117 | 113 | 137 | 128 |
| | | 44 | 66 | 69 | 80 | 72 |
| | | 61 | 128 | 135 | 124 | 208 |
| | | 82 | 91 | 93 | 85 | 148 |
| | | 86 | 182 | 169 | 166 | 178 |
| Pseudomonas aeruginosa | Ps- | 87 | 83 | 86 | 67 | 86 |
| | | 88 | 78 | 87 | 57 | 148 |

TABLE II-continued

EFFECT OF CONCENTRATION ON SELECTIVITY OF BASAL AGAR MEDIUM FOR *PSEUDOMONAS AERUGINOSA* UPON CHALLENGE INOCULATION WITH SOME NON-PSEUDOMONAO STRAINS AS DETERMINED BY AVERAGE COLONY COUNTS

| Test Microogranism | Culture Code | No. | Selective (μg/ml) Basal Medium 20 | 25 | 30 | Non-Selective TSA[1] Control |
|---|---|---|---|---|---|---|
|  |  | 89 | 102 | 97 | 122 | 93 |
|  |  | 90 | 2 | 2 | 2 | 6 |
|  |  | 91 | 82 | 68 | 59 | 67 |
|  |  | 92 | 176 | 160 | 154 | 125 |
|  |  | 93 | 236 | 227 | 191 | 285 |
| *Enterobacter aerogenes* |  | 34 | 0 |  |  | 83 |
|  |  | 63 | 0 | 0 | 0 | 190 |
|  |  | 67 | 8 |  |  | 425 |
| *Enterobacter cloacae* | Ae- | 8 | 36 | 1 |  | 296 |
|  |  | 62 | 2 | 0 |  | 111 |
|  |  | 65 | 0 | 0 | 0 | 95 |
|  |  | 66 | 3 | 0 |  | 246 |
| *Serratia marcescens* | Se- | 2 | 0 | 0 |  | 128 |
|  |  | 4 | 0 | 0 |  | 248 |
|  |  | 6 | 0 | 0 | 0 | 181 |
|  |  | 9 | 0 | 0 |  | 303 |
|  |  | 13 | ND[2] | 0[3] |  | 213 |

[1]Trypticase Soy Agar
[2]Not Done
[3]Count from 1 plate

In order that this invention may be readily available to and understood by those skilled in the art, the now preferred method for its preparation is briefly described:

A. Preparation of 9)p-Diethylaminophenyl)-9-Methoxy-10-Phenylacridan

N,N-diphenylanthranilic acid (10 g, 0.0346 mole), diethylaniline (12.3 g, 0.0826 mole) and 100 ml of toluene are placed in a 250 ml three-necked flask fitted with an overhead stirrer, thermometer, dropping funnel and a condenser. Stirring is initiated while phosphorus oxychloride (25 g, 0.1629 mole) is added dropwise over a five-minute period. The reaction temperature rises from 26° C. to 36° C. during the addition of the first 60% of the POCl$_3$ and drops slowly as the remaining 40% of the POCl$_3$ is added. The reaction is heated to reflux (108° C.) and held there for three hours.

The solvent and excess POCl$_3$ is then distilled from the reaction flask until a pot temperature of 140° C. is reached. The total distillate weights 93.8 g.

The pot residue is cooled to 50° C. and 180 ml of anhydrous methanol is added. With cooling 10 g of sodium hydroxide pellets is added. The dark green solution turns purple and then colorless. An additional 3 g of sodium hydroxide pellets is added to completely remove the purple color. The slurry is refluxed for 40 minutes, cooled to 20° C. and the solids collected on a Buchner funnel. The solids are washed with 20 ml of methanol and then reslurried in 150 ml of hot water followed by refiltering. The filter cake is washed with hot water, cold water and then with 20 ml of cold methanol. The product is air-dried to give 12.0 g (80% yield) of 9-(p-diethylaminophenyl)-9-methoxy-10-phenylacridan.

B. Preparation of 9(p-Diethylaminophenyl)-9-Chloro-10-Phenylacridan

9(p-Diethylaminophenyl)-9-methoxy-10-phenylacridan (12.0 g, 0.0276 mole) is slurried in 150 ml of tetrahydrofuran while anhydrous hydrogen chloride is bubbled in with cooling. The hydrogen chloride is bubbled in until the slurry reaches a pH of 1.0 and a bright yellow color is obtained. The product is collected on a Buchner funnel, washed twice with 10 ml portions of tetrahydrofuran and dried at 50° C. to give 11.6 g (95.8% yield) of 9(p-diethylaminophenyl)-9-chloro-10-phenylacridan.

What is claimed is:

1. An agar medium for the selective isolation of *Pseudomonas aeruginosa* from other bacterial species containing 30 μg./ml. of 9-(p-diethylaminophenyl)-9-chloro-10-phenylacridan.

* * * * *